(12) United States Patent
McKee et al.

(10) Patent No.: US 10,293,086 B2
(45) Date of Patent: May 21, 2019

(54) FLUOROPOLYMER COATINGS AND RELATED METHODS

(71) Applicant: Merit Medical Systems, Inc., South Jordan, UT (US)

(72) Inventors: William Paul McKee, Heeze (NL); Albert Hillen, Nuth (NL); Pieter van der Wal, Venlo (NL)

(73) Assignee: Merit Medical Systems, Inc., South Jordan, UT (US)

( * ) Notice: Subject to any disclaimer, the term of this patent is extended or adjusted under 35 U.S.C. 154(b) by 116 days.

(21) Appl. No.: 15/130,569

(22) Filed: Apr. 15, 2016

(65) Prior Publication Data

US 2016/0303292 A1    Oct. 20, 2016

Related U.S. Application Data

(60) Provisional application No. 62/148,605, filed on Apr. 16, 2015.

(51) Int. Cl.
*A61L 29/04* (2006.01)
*A61L 31/10* (2006.01)
(Continued)

(52) U.S. Cl.
CPC .............. *A61L 31/10* (2013.01); *A61L 29/049* (2013.01); *A61L 29/06* (2013.01); *A61L 29/085* (2013.01);
(Continued)

(58) Field of Classification Search
CPC .......... C08L 81/06; C08L 79/08; C08L 27/12; C08L 27/14; C08L 27/16; C08L 27/18; C08L 27/20; C09D 181/06; C09D 179/08; C09D 127/12; C09D 127/14; C09D 127/16; C09D 127/18; C09D 127/20; C09J 181/06; C09J 179/08; C09J 127/12; C09J 127/14; C09J 127/16; C09J 127/18; C09J 127/20; C08J 2381/06; C08J 2379/08; C08J 2327/12; C08J 2327/14; C08J 2327/16;
(Continued)

(56) References Cited

U.S. PATENT DOCUMENTS 3,708,458 A * 1/1973 Alberino ............ C08G 73/1042
528/222
4,803,147 A    2/1989 Mueller et al.
(Continued)

FOREIGN PATENT DOCUMENTS

WO    199317077    9/1993
WO    2006127763    11/2006

OTHER PUBLICATIONS

Ellis et al., Polymers: A Property Database (2009).*
(Continued)

*Primary Examiner* — Kregg T Brooks
(74) *Attorney, Agent, or Firm* — Stoel Rives LLP

(57) ABSTRACT

A coating for a medical device or appliance may include a fluoropolymer and a polyimide. Such coatings may provide a lubricious exterior surface that facilitates insertion or displacement of a medical device in a body lumen. Some coatings that include a fluoropolymer and a polyimide may, among other functions and characteristics, provide increased strength and/or durability relative to some other coatings.

18 Claims, 3 Drawing Sheets

(51) Int. Cl.
| | |
|---|---|
| *A61L 29/06* | (2006.01) |
| *A61L 29/08* | (2006.01) |
| *A61L 31/04* | (2006.01) |
| *B05D 1/18* | (2006.01) |
| *B05D 1/38* | (2006.01) |
| *C09D 123/28* | (2006.01) |
| *C09D 179/08* | (2006.01) |
| *C09D 181/06* | (2006.01) |
| *C09D 127/12* | (2006.01) |
| *C09D 127/18* | (2006.01) |
| *C09D 127/20* | (2006.01) |
| *C09D 127/14* | (2006.01) |
| *C09D 127/16* | (2006.01) |
| *B05D 5/08* | (2006.01) |
| *B05D 7/00* | (2006.01) |

(52) U.S. Cl.
CPC ........... *A61L 31/041* (2013.01); *A61L 31/048* (2013.01); *B05D 1/38* (2013.01); *C09D 127/12* (2013.01); *C09D 127/14* (2013.01); *C09D 127/16* (2013.01); *C09D 127/18* (2013.01); *C09D 127/20* (2013.01); *C09D 179/08* (2013.01); *C09D 181/06* (2013.01); *A61L 2400/12* (2013.01); *A61L 2420/02* (2013.01); *A61L 2420/06* (2013.01); *A61L 2420/08* (2013.01); *B05D 1/18* (2013.01); *B05D 5/083* (2013.01); *B05D 7/50* (2013.01); *B05D 2202/15* (2013.01); *B05D 2254/02* (2013.01); *B05D 2256/00* (2013.01); *B05D 2505/50* (2013.01); *B05D 2506/15* (2013.01); *B05D 2518/00* (2013.01)

(58) Field of Classification Search
CPC .............. C08J 2327/18; C08J 2327/20; C08G 73/1042; C08G 73/1067; A61L 31/10; A61L 31/041; A61L 31/048; A61L 29/049; A61L 29/06; A61L 29/085; A61L 2420/06; A61L 2420/08; B32B 27/28; B32B 27/281; B32B 27/286; B05D 5/083
See application file for complete search history.

(56) References Cited

U.S. PATENT DOCUMENTS

| | | | |
|---|---|---|---|
| 5,582,886 A | 12/1996 | Kitajima et al. | |
| 6,213,995 B1 | 4/2001 | Steen et al. | |
| 7,462,667 B2 | 12/2008 | Dadalas et al. | |
| 7,488,304 B2 | 2/2009 | Goodin et al. | |
| 7,627,382 B2 | 12/2009 | Minar et al. | |
| 2004/0110011 A1* | 6/2004 | Shah | B05D 5/083 428/421 |
| 2008/0008838 A1* | 1/2008 | Arpac | C08G 18/3812 427/386 |
| 2010/0217372 A1 | 8/2010 | Lentz | |
| 2011/0138852 A1 | 6/2011 | Hasse et al. | |
| 2012/0223014 A1 | 9/2012 | Boam et al. | |
| 2013/0197497 A1* | 8/2013 | Wittenberger | A61B 18/02 606/21 |
| 2016/0068670 A1* | 3/2016 | Hosoda | H01B 13/14 428/375 |

OTHER PUBLICATIONS

CRC Handbook of Mechanical Engineering (2004).*
Mordfin et al., Handbook of Reference Data for Nondestructive Testing (2002) ("Mordfin").*
Evonik Industries, Polyimide P84 NT, Technical Brochure, No date available.
P84 Polyimide, PTFE/Polyimide Compound, HP Polymer GmbH, 1997.
Polyimide P84 NT1 Powder, Evonik Industries, Material Safety Data Sheet, Mar. 2, 2014.
International Search Report and Written Opinion dated Jul. 28, 2016 for PCT/US2016/027861.
European Search Report dated Nov. 13, 2018 for EP16780884.9.

* cited by examiner

FLUOROPOLYMER COATINGS AND RELATED METHODS

RELATED APPLICATIONS

This application claims the benefit of U.S. Provisional Application No. 62/148,605, filed on Apr. 16, 2015 and titled, "FLUOROPOLYMER COATINGS AND RELATED METHODS," which is hereby incorporated by reference in its entirety.

TECHNICAL FIELD

The present disclosure relates generally to the field of coatings, and more particularly to coatings for medical appliances or devices. Related methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Elongate medical instruments, such as guidewires, hypotubes, stylets etc., are often inserted into a patient for diagnostic or therapeutic procedures. Such medical instruments may include a coating that imparts one or more characteristics or properties to the medical instrument. For instance, a coating may affect, among other properties or characteristics, the biocompatibility, chemical resistance, elasticity, durability, and/or lubricity of a medical instrument.

In some embodiments disclosed herein, a coating for a medical instrument may include a polymer blend that comprises a fluoropolymer (e.g., polytetrafluoroethylene (PTFE)) and a polyimide, such as an aromatic polyimide. Relative to at least some fluoropolymer coatings that lack a polyimide, coatings that include both a fluoropolymer and a polyimide may exhibit increased durability. Increased durability may render a medical instrument less susceptible to wear as a result of use in a medical procedure. Accordingly, increased durability may prevent the medical instrument from changing in a significant and/or detrimental way during a medical procedure. For example, increased durability may decrease the extent to which an outermost layer of a coating is scratched or removed. Removal of an outermost layer may affect one or more properties of the medical instrument, such as by decreasing the lubricity of the medical instrument. Other distinguishing features of embodiments described herein will be apparent to one of ordinary skill in the art having the benefit of this disclosure.

The components of the embodiments as generally described and illustrated herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The terms "coat" and "layer" may be used interchangeably to refer to a layer of a coating. Unless otherwise stated, all ranges include both endpoints and all numbers between the endpoints. The experimental conditions for determining the dynamic coefficients of friction recited and claimed herein are set forth in Example 11. Other coefficient of friction values are possible when measured under different conditions.

Figure 1:
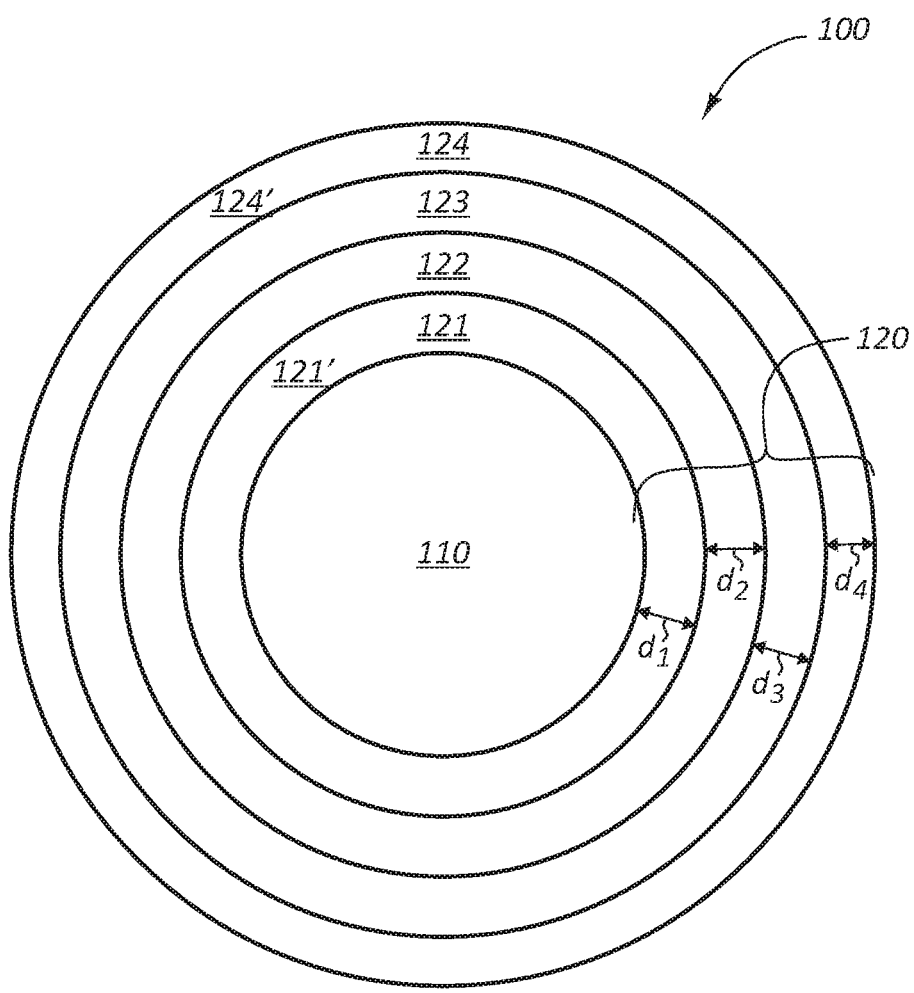
FIG. 1 is a cross-sectional view of a medical appliance.

FIG. 1 provides a cross-sectional view of a coated medical appliance 100. In the depicted embodiment, the coated medical appliance 100 is depicted as a coated guidewire. However, other coated appliances, such as coated hypotubes, stylets, mandrels etc. are within the scope of this disclosure. The coated medical appliance 100 may include a substrate 110 (e.g., a wire) and a coating 120 that forms an outer surface of the medical appliance 100. In the depicted embodiment, the coating 120 is a multilayer coating that comprises a first layer 121, a second layer 122, a third layer 123, and a fourth layer 124. Stated differently, when viewed as depicted in FIG. 1, the layers 121, 122, 123, 124 may form a series of concentric rings around the substrate 110. In the depicted embodiment, each layer is immediately adjacent to at least one other layer. For example, the first layer 121 is immediately adjacent to the second layer 122, and the second layer 122 is immediately adjacent to both the first layer 121 and the third layer 123. In some embodiments, each layer 121, 122, 123, 124 is macroscopically homogeneous.

In other embodiments, a coated medical appliance may have less than four layers. For example, a coated medical appliance may have only one, two, or three layers or coats. In still other embodiments, the coated medical appliance may have more than four layers.

In the depicted embodiment, the first layer 121 is an innermost layer 121' that is configured to adhere directly to a substrate 110, such as a wire. Stated differently, the innermost layer 121' may be configured to adhere directly to a metal or metallic alloy of the substrate 110, such as stainless steel, nitinol, or copper.

In the depicted embodiment, the fourth layer 124 is an outermost layer 124'. In some embodiments, the outermost layer 124' provides a lubricious exterior surface. The lubricious exterior surface may facilitate advancement and/or withdrawal of the medical appliance 100 (e.g., a guidewire) within a lumen of the patient. In some embodiments, the outer surface of the medical appliance 100 has an average dynamic coefficient of friction that is less than or equal to about 0.40, about 0.35, about 0.30, about 0.25, about 0.20, about 0.17, about 0.15, and/or about 0.14. In some embodiments, the outer surface has an average dynamic coefficient of friction of between about 0.06 and about 0.40, about 0.10 and about 0.40, about 0.10 and about 0.35, about 0.10 and about 0.30, about 0.11 and about 0.25, about 0.12 and about 0.20, about 0.12 and about 0.17, and about 0.12 and about 0.15, and/or about 0.12 and about 0.14.

In some embodiments, the composition of each layer is substantially the same as the composition of other layers. In other embodiments, the composition of one or more layers may differ from the composition of one or more other layers.

In some embodiments, a coating 120 comprises one or more primer layers 121, 122, 123. Such primer layers 121, 122, 123 may include a polyethersulfone. Stated differently, in some embodiments, one or more layers 121, 122, 123, 124 include a polyethersulfone. For instance, one or more layers 121, 122, 123, 124, when dried, may be more than about 10%, about 20%, about 30%, about 40%, about 50%, about 60%, about 70%, about 80%, about 90% and/or about 95% polyethersulfone by weight. Some layers that include a polyethersulfone may be substantially devoid of fluoropolymers and/or polyimides. In some embodiments, a layer that includes a polyethersulfone may also include a colorant (e.g., a dye or pigment) that imbues that layer with a particular color (e.g., black, green, grey, blue, etc.). In some embodiments, the uniformity of color for a coating 120 may be increased by applying a plurality of pigment-containing primer layers 121, 122, 123.

In some embodiments, the innermost layer 121' of a coating 120 may comprise a polyethersulfone. An innermost layer 121' may be configured to adhere to a substrate 110 in any suitable fashion. Further, in some embodiments, the composition of the innermost layer 121', which may include a polyethersulfone, is configured to adhere to the substrate 110 better than the composition of one or more other layers 122, 123, 124 of the coating 120.

In some embodiments, one or more layers 121, 122, 123, 124 may include one or more of a polyimide and/or a polyamide. For example, a layer may include an aromatic and/or aliphatic polyimide. For instance, a layer may include a polyimide that comprises a subunit defined by Formula I:

Formula I

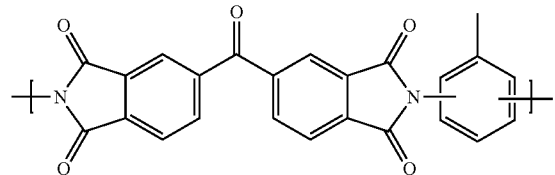

In other or further embodiments, the polyimide comprises a subunit defined by Formula II:

Formula II

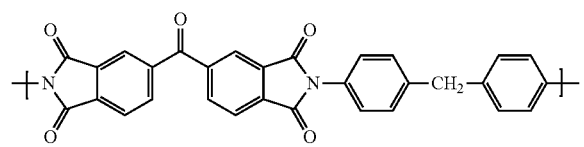

For instance, in some embodiments, one or more layers 121, 122, 123, 124 may include copolymer I. Copolymer I can be represented by Formulas I and II, wherein copolymer I comprises about 10% to about 90% (e.g., about 60% to about 90%) of the subunit defined by Formula I and about 10% to about 90% (e.g., about 10% to about 40%) of the subunit defined by Formula II. The copolymer may be formed by the co-condensation of di(4-aminophenyl) methane and toluene diamine with benzophenone 3,3',4,4'-tetrac-arboxylic acid dianhydride. Other methods of preparing copolymer I are also possible. In some embodiments, the polyimide consists essentially of subunits defined by Formula I and subunits defined by Formula II. In some embodiments, the ratio of subunits defined by Formula I compared to the subunits defined by Formula II is between about 10:1 and about 1:1, between about 7:1 and about 2:1, and/or between about 5:1 and about 3:1. Other polyimides, such as the polyimide defined by Formula III, i.e., poly(4,4'-oxydiphenylene-pyromellitimide) (e.g., Kapton®), may also be used.

Formula III

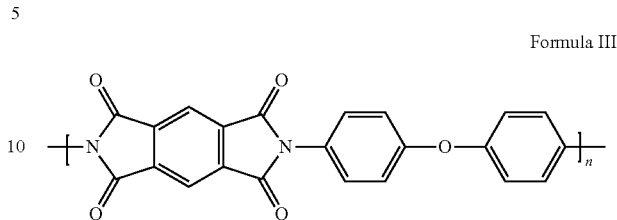

In some embodiments, one or more layers (e.g., an outer layer) may consist essentially of the polyimide defined by Formula III. In other or further embodiments, the polyimide may include the substructure of Formula IV.

Formula IV

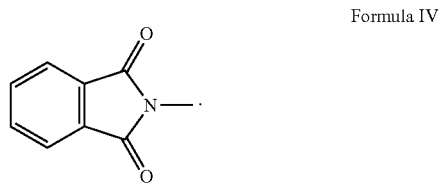

A polyimide may be supplied in any suitable form, such as a powder or a fiber, before being applied to a substrate 110.

In some embodiments, one or more layers 121, 122, 123, 124 may include a polymer blend that includes both a polyethersulfone and a polyimide. Any suitable ratio of polyethersulfone to polyimide may be used. For example, for some layers the mass fraction of polyethersulfone to polyimide may be between any of about 10:1 and about 1:10, about 10:1 and about 1:1, about 5:1 and about 3:2, and/or about 3:1 and about 1:1.

In some embodiments, one or more layers 121, 122, 123, 124 include a fluoropolymer, such as PTFE. More particularly, in some embodiments, one or more layers 121, 122, 123, 124 include both a fluoropolymer and a polyimide. For example, a layer, such as outermost layer 124', may include a polymer blend that comprises both a fluoropolymer and a polyimide. In some embodiments, the polymer blend is between about 50% and about 95% fluoropolymer, between about 70% and about 90% fluoropolymer, between about 70% and about 80% fluoropolymer, between about 80% and about 90% fluoropolymer, and/or between about 80% and about 95% fluoropolymer by weight. In other or further embodiments, the polymer blend is between about 5% and about 50% polyimide, about 15% and about 50% polyimide, about 5% and about 20% polyimide, about 10% and about 30% polyimide, about 20% and about 30% polyimide, and/or about 10% and about 20% polyimide by weight. The mass fraction of fluoropolymer to polyimide in an outermost layer 124' may be between any of about 10:1 and about 1:2, about 5:1 and about 1:1, about 8:1 and about 2:1, about 8:1 and about 6:1, or about 4:1 and about 2:1. For example, the mass fraction of fluoropolymer to polyimide may be approximately 7:1 or 3:1. In some embodiments, the polymer blend comprises more fluoropolymer than polyethersulfone by dry weight. A layer having a polymer blend that includes both a fluoropolymer and a polyimide may differ in one or more respects relative to an analogous layer that includes a fluoropolymer, but lacks a polyimide. For example, a layer that includes both a fluoropolymer and a polyimide may be stronger and/or more durable than a layer that includes a fluoropolymer but not a polyimide. In some embodiments, the elastic and/or flexural modulus of the polyimide is greater than the elastic and/or flexural modulus of the fluoropolymer.

In some embodiments, one or more layers 121, 122, 123, 124 may include a polymer blend that comprises a fluoropolymer, a polyimide, and a polyethersulfone. A polymer blend that includes a fluoropolymer, a polyimide, and a polyethersulfone may differ in one or more respects relative to a layer that includes a fluoropolymer and a polyethersulfone, but not a polyimide. For example, a layer that includes a fluoropolymer, a polyethersulfone, and a polyimide may be stronger and/or more durable than a layer that includes a fluoropolymer and a polyethersulfone, but not a polyimide.

In some embodiments, one or more layers 121, 122, 123, 124 may include a polyamide-imide, such as Torlon®. For example, in some embodiments, a layer may include a polyamide-imide and a fluoropolymer, such as PTFE. In further embodiments, a layer may include a polyamide-imide, a fluoropolymer, and a polyimide (e.g., copolymer I). In some embodiments, a layer that includes a polyamide-imide may be disposed between an outermost layer 124' and an innermost layer 121'. For example, in some embodiments, a polyamide-imide-containing layer 123 may function as a "binder layer." When a layer 123 is a binder layer, the layers 122 and 124 adjacent to the binder layer 123 adhere better to the binder layer 123 than they do to each other. Binder layers that lack a polyamide-imide are also possible. Some coatings 120 may include one layer that includes a polyamide-imide and a different layer than includes a polyimide that differs from the polyamide-imide. The layer that includes the polyimide that differs from the polyamide-imide may be less than or equal to about 50%, about 40%, about 30%, about 20%, about 17%, about 15% and/or about 12.5% polyimide by weight. In other or further embodiments, the layer that includes a polyimide that differs from the polyamide-imide is greater than or equal to about 2%, about 5%, and/or about 10% polyimide by weight. In some embodiments, the outermost layer 124' lacks a polyamide-imide.

Each layer of the coating 120 may have any suitable thickness. For example, some layers (e.g., innermost layer 121') have a thickness ($d_1$) of between about 0.75 μm and about 2.0 μm, about 1 μm and about 2 μm, and/or between about 1.2 μm and about 1.5 μm. In some embodiments, an outermost layer 124' may be thinner than any other layer 121, 122, 123 of a coating 120. In some embodiments, the outermost layer 124' has a thickness ($d_4$) of between any of about 0.25 μm and about 1.2 μm, about 0.5 μm and about 1.2 μm, about 0.25 μm and about 0.75 μm, about 0.60 μm and about 1.0 μm, and/or between about 0.40 μm and about 0.70 μm. In some embodiments, one or more of the layers 122, 123 disposed between the outermost layer 124' and the innermost layer 121' may have a thickness ($d_2$, $d_3$) of between about 0.5 μm and about 2.6 μm, about 0.8 μm and about 2.6 μm, about 0.5 μm and about 1.5 μm and/or about 1.0 μm and about 1.5 μm. In some embodiments, the entire coating 120 (e.g., the four-layer coating in FIG. 1) has a total thickness of between about 4 μm and about 8 μm, such as between about 4.5 and about 5.5 μm.

In some embodiments, the first two layers 121, 122 each comprise a polyethersulfone. For example, such layers 121, 122 may be greater than or equal to about 50%, about 60%, about 70%, about 80%, and/or about 90% polyethersulfone by weight. Such layers 121, 122 may be substantially devoid of a fluoropolymer or a polyimide. In further embodiments, the third layer 123 may include a polyethersulfone and a polyimide, such as copolymer 1. The third layer 123 may also be substantially devoid of a fluoropolymer. In some instances, the fourth layer 124 of such embodiments may include a fluoropolymer (e.g., PTFE), a polyethersulfone, and a polyimide (e.g., copolymer I or poly(4,4'-oxydiphenylene-pyromellitimide)).

Embodiments in which an outermost layer 124' includes a fluoropolymer and a polyimide may differ in one or more respects from embodiments with an outermost layer that lacks (or has relatively low amounts of) one or more of a fluoropolymer and a polyimide. For example, an outermost layer 124' that includes a fluoropolymer and a polyimide may have improved wear resistance, adhesion, cohesion, strength, and/or durability relative to some outermost layers that lack (or have relatively low amounts of) a fluoropolymer and/or a polyimide. In some embodiments, an outermost layer 124' that includes a fluoropolymer and a polyimide may be sufficiently lubricious for delivery and/or withdrawal of a coated elongate medical appliance 100 (e.g., a guidewire) into and/or from the vasculature of a patient. Stated differently, an outermost layer 124' that includes a fluoropolymer and a polyimide may have an average dynamic coefficient of friction that is comparable to or lower than that of (1) a PTFE-only outermost layer and/or (2) an outermost layer comprising only a polymer blend that consists essentially of PTFE and polyethersulfone.

In some embodiments, the inclusion of a polyimide in a layer may affect the adhesive properties of the layer. For example, the addition of a polyimide to an outermost layer 124' may promote improved adhesion with an underlying layer, such as third layer 123. The inclusion of a polyimide in other layers, such as third layer 123, may promote adhesion to an adjacent layer, such as second layer 122.

In some embodiments, the inclusion of a polyimide in a layer may likewise affect the cohesive properties of the layer. Stated differently, portions of a layer that include a polyimide may be less likely to wear off of that layer due to chemical treatment and/or abrasive forces. The inclusion of a polyimide in a layer may also reduce the amount of particulate that accumulates on a coating 120 as a result of manufacture of a coated medical appliance 100.

In some embodiments, the inclusion of a polyimide in a layer may affect (e.g., improve) the uniformity of color in a layer 121, 122, 123, 124 or coating 120. In some embodiments, the one or more layers 121, 122, 123, 124 of a coating 120 are substantially devoid of metallic filler. For example, in some embodiments, the entire coating 120 is substantially devoid of metallic filler. In some embodiments, one or more layers 121, 122, 123, 124 may lack abrasive material. For instance, in some embodiments, the entire coating 120 is substantially devoid of abrasive material.

Coated medical appliances, such as those described in connection with FIG. 1, may be manufactured in any suitable manner. For example, in some embodiments, each layer 121, 122, 123, 124 of an elongate medical appliance 100 may be applied to an elongate substrate using a spool-to-spool process. In other words, a layer may be applied to an elongate substrate 110 as the elongate substrate 110 is drawn from a "payoff" spool and wound onto a "take-up" spool. For example, a first solution may be applied to the elongate substrate 110 by passing the elongate substrate 110 through one or more vessels that contain the first solution. As the coated elongate substrate 110 emerges from the vessel, the elongate substrate 110 may pass through a die that meters the volume of material that is applied to the elongate substrate 110. The elongate substrate 110 may then be exposed to elevated temperature(s) to remove at least a portion of the solvent. Elevated temperature(s) may also sinter or otherwise cure the applied layer. Exposure to elevated temperature(s) may be accomplished by passing the elongate substrate 110 through an oven, such as a multi-zone oven. The temperature(s) for each zone may be configured to control the rate and/or extent of solvent removal.

After a first layer 121 has been applied, a second layer 122 may be applied over the first layer 121 in an analogous manner. In other words, an elongate substrate 110 to which a first layer 121 has been applied may again be drawn through a vessel containing a second solution to be applied to the elongate substrate. In some embodiments, the second solution is substantially identical to the first solution. In other embodiments, the second solution differs in one or more respects from the first solution. Once the second layer 122 has been applied to the first layer 121, the second layer 122 may be cured and/or dried in a manner analogous to that described above in connection with the first layer 121. Additional layers, such as a third layer 123 and a fourth layer 124, may be applied, cured, and/or dried in an analogous manner.

In some embodiments, once the final layer (e.g., outermost layer 124') has been applied, the medical appliance 100 may be subjected to one or more additional processing steps. For example, in some embodiments, the medical appliance 100 (or a portion thereof) is subjected to infrared radiation. In other embodiments, the medical appliance 100 is not subjected to infrared radiation. The resulting medical appliance 100 may be stored in a spooled form.

While the coating 120 of FIG. 1 is described above as a coating 120 for a wire, analogous coatings may be applied to other substrates, such as a hypotube, a stylet, a mandrel, or any other appliance (e.g., an elongate medical appliance).

Figure 2:
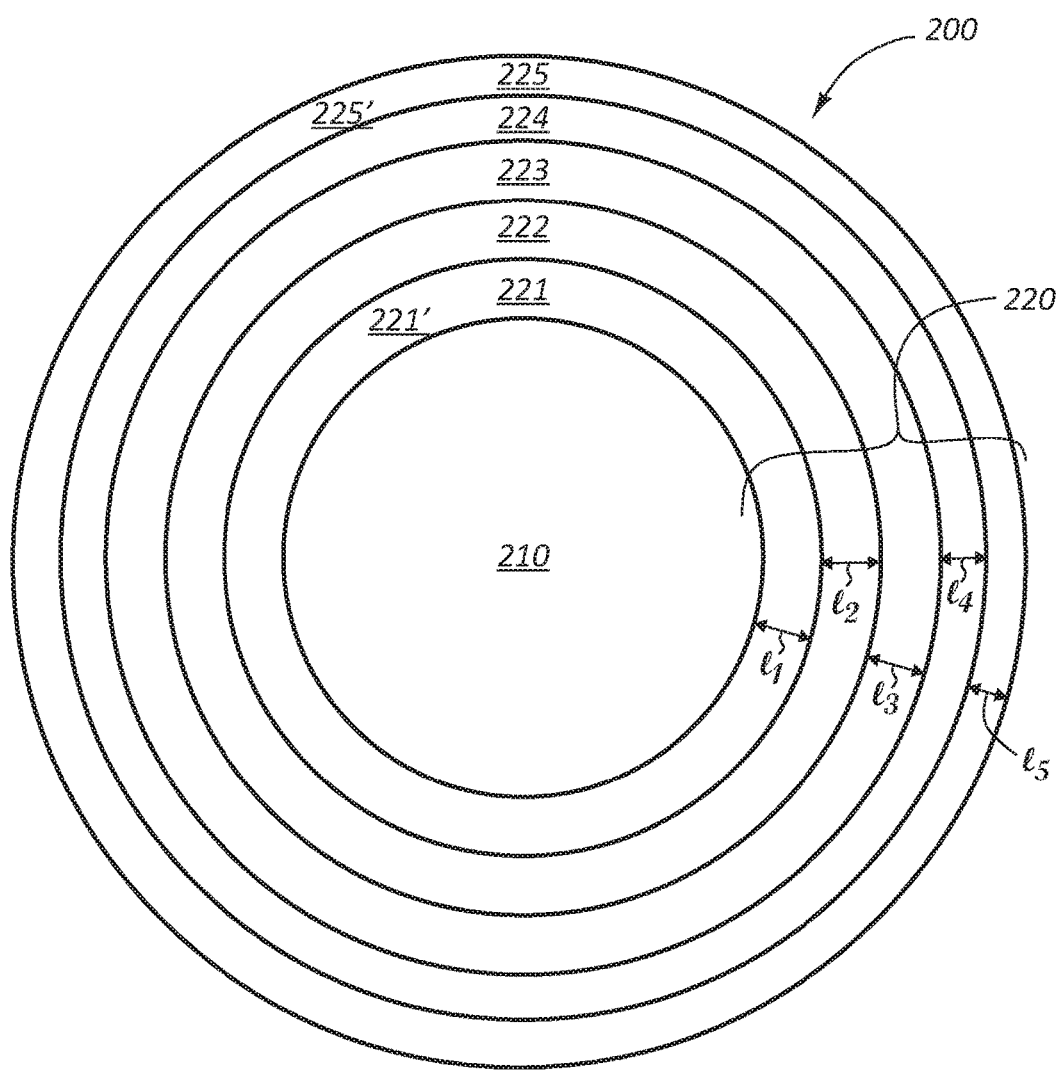
FIG. 2 is a cross-sectional view of a medical appliance, according to another embodiment.

FIG. 2 depicts an embodiment of a medical appliance 200 that resembles the coated medical appliance 100 described above in certain respects. Accordingly, like features are designated with like reference numerals, with the leading digits incremented to "2." For example, the embodiment depicted in FIG. 2 includes an elongate substrate 210 that may, in some respects, resemble the elongate substrate 110 of FIG. 1. Relevant disclosure set forth above regarding similarly identified features thus may not be repeated hereafter. Moreover, specific features of medical appliances and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical appliance 200 and related components depicted in FIG. 2. Any suitable combination of the features, and variations of the same, described with respect to the medical appliance 100 and related components illustrated in FIG. 1 can be employed with the medical appliance 200 and related components of FIG. 2, and vice versa.

FIG. 2 provides a cross-sectional view of a coated medical appliance 200. The medical appliance 200 includes a substrate 210 and a coating 220 that forms an outer surface of the medical appliance 200. In the depicted embodiment, the substrate 210 is a wire. However, analogous coatings may be applied to other medical appliances, such as hypotubes, stylets, etc. In the depicted embodiment, the coating 220 is a multilayer coating that comprises a first layer 221, a second layer 222, a third layer 223, a fourth layer 224, and a fifth layer 225. Stated differently, when viewed as depicted in FIG. 2, the layers 221, 222, 223, 224, 225 may form a series of concentric rings around the substrate 210. In the depicted embodiment, each layer is immediately adjacent to at least one other layer. For example, the first layer 221 is immediately adjacent to the second layer 222, and the second layer 222 is immediately adjacent to both the first layer 221 and the third layer 223. One of ordinary skill in the art, with the benefit of this disclosure, will recognize that other embodiments within the scope of this disclosure may include more or less than five layers.

One or more layers 221, 222, 223, 224, 225 of the coating 220 may resemble one or more layers 121, 122, 123, 124 described above in connection with the coating 120 of FIG. 1. For example, the first layer 221 (i.e., innermost layer 221') may be configured to adhere directly to an elongate substrate 210, such as a wire. In some embodiments, the substrate 210 comprises a metal or metallic alloy, such as stainless steel, nitinol, and/or copper.

The coating 220 may include an outermost layer 225'. The outermost layer 225' may provide a lubricious exterior surface. The lubricious exterior surface provided by the outermost layer 225' may facilitate insertion and/or withdrawal of the medical appliance 200 into and/or from a patient. In some embodiments, the outermost layer 225' has an average dynamic coefficient of friction that is less than or equal to about 0.40, about 0.35, about 0.30, about 0.25, about 0.20, about 0.17, about 0.15, and/or about 0.14. In some embodiments, the outer surface has an average dynamic coefficient of friction of between about 0.10 and about 0.40, about 0.10 and about 0.35, about 0.10 and about 0.30, about 0.11 and about 0.25, about 0.12 and about 0.20, about 0.12 and about 0.17, about 0.12 and about 0.15, and/or about 0.12 and about 0.14.

In some embodiments, the composition of one or more layers may differ from the composition of one or more other layers. The compositions for different layers may be tailored to impart desired characteristics to the medical appliance 200. For example, in some embodiments, the composition of an innermost layer 221' may be selected to promote adhesion to a substrate 210. An outermost layer 225' may be selected to provide durability and/or lubricity. The composition of other layers 222, 223, 224 may be selected based on any number of criteria, such as to promote adhesion between layers, and/or provide more uniform color to the elongate medical appliance 200. In some embodiments, one or more layers have the same (or substantially the same) composition as one or more other layers.

In some embodiments, one or more layers 221, 222, 223, 224, 225 include a polyethersulfone. For instance, in some embodiments, one or more layers 221, 222, 223, 224, 225, when dried, may be more than about 10%, about 20%, about 30%, about 40%, about 50%, about 60%, about 70%, about 80%, about 90% and/or about 95% polyethersulfone by weight. Some layers that include a polyethersulfone may be substantially devoid of fluoropolymers and/or polyimides. In some embodiments, a layer that includes a polyethersulfone may also include a colorant (e.g., a dye or pigment) that imbues that layer with a particular color (e.g., black, green, grey, blue, etc.).

In some embodiments, the innermost layer 221' comprises a polyethersulfone. An innermost layer 221' may lack or have relatively low amounts of fluoropolymers and/or polyimides. An innermost layer 221' may be configured to adhere to a substrate 210 in a suitable fashion. Indeed, in some embodiments, the composition of the innermost layer 221', which may include a polyethersulfone, is configured to adhere to the substrate 210 better than the composition of one or more other layers 222, 223, 224, 225 of the coating 220.

In some embodiments, one or more layers 221, 222, 223, 224, 225 may include a polyimide, such as one or more of the polyimides described above in connection with FIG. 1. In some embodiments, one or more layers 221, 222, 223, 224, 225 include a polymer blend that comprises a polyethersulfone and a polyimide. Any suitable ratio of polyethersulfone to polyimide may be used. For example, the mass fraction of polyethersulfone to polyimide may be, for some layers, between about 10:1 and about 1:10, about 10:1 and about 1:1, about 5:1 and about 3:2 and/or about 3:1 to about 2:1.

In some embodiments, one or more layers 221, 222, 223, 224, 225 include a fluoropolymer, such as PTFE. For instance, some layers 221, 222, 223, 224, 225 may include a polymer blend that comprises both a fluoropolymer and a polyimide. In some embodiments, the polymer blend is between about 50% and about 95% fluoropolymer, between about 70% and about 90% fluoropolymer, between about 70% and about 80% fluoropolymer, between about 80% and about 90% fluoropolymer, and/or between about 80% and about 95% fluoropolymer by weight. In other or further embodiments, the polymer blend is between about 5% and about 50% polyimide, about 15% and about 50% polyimide, about 5% and about 20% polyimide, about 10% and about 30% polyimide, about 20% and about 30% polyimide, and/or about 10% and about 20% polyimide by weight. The mass fraction of fluoropolymer to polyimide in a layer, such as outer layer 225' may be between about 10:1 and 1:1, about 8:1 and 2:1, about 8:1 and 6:1, about 4:1 and 2:1. For example, the mass fraction of fluoropolymer to polyimide may be approximately 7:1 or 3:1. In some embodiments, the polymer blend comprises more fluoropolymer than polyethersulfone by dry weight. Layers that include both a fluoropolymer and a polyimide may be stronger and/or more durable than an analogous layer that lacks (or has a relatively lower amount of) a polyimide, such as a 100% PTFE layer. Such a layer may also differ in other respects relative to a layer that includes a fluoropolymer but lacks a polyimide. In some embodiments, an outermost layer 225' comprises a fluoropolymer and a polyimide.

In some embodiments, one or more layers 221, 222, 223, 224, 225 may include a polyamide-imide, such as Torlon®. For example, in some embodiments, a layer 221, 222, 223, 224, 225 includes a polyamide-imide and a fluoropolymer, such as PTFE. In other or further embodiments, a layer 221, 222, 223, 224, 225 may include a polyamide-imide, a fluoropolymer, and a polyimide (e.g., copolymer I) that differs from the polyamide-imide. In some embodiments, a layer that includes a polyamide-imide may be disposed between an outermost layer 225' and an innermost layer 221'. For example, in some embodiments, the layer adjacent to the outermost layer 225' (e.g., layer 224 of the depicted embodiment) may include a polymer blend that comprises a polyamide-imide, a fluoropolymer (e.g., PTFE), and a polyimide (e.g., copolymer I). In some embodiments that include a polyamide-imide and a polyimide that differs from the polyamide-imide, the polyimide (e.g., copolymer I) may comprise less than or equal to about 50%, about 40%, about 30%, about 20%, about 17%, about 15% and/or about 12.5% polyimide by weight. In other or further embodiments, the layer that includes a polyimide that differs from the polyamide-imide is greater than or equal to about 2%, about 5%, and/or about 10% polyimide by weight. In some embodiments, the outermost layer 225' lacks a polyamide-imide.

Each layer 221, 222, 223, 224, 225 of a coating 220 may have any suitable thickness. For example, some layers (e.g., innermost layer 221') may have a thickness ($I_1$) of between about 0.75 µm and about 2 µm, about 1 and about 2 µm, and/or about 1.2 and about 1.5 µm. In some embodiments, an outermost layer 225' may be thinner than any other layer 221, 222, 223, 224 of a coating 220. In some embodiments, the outermost layer 225' has a thickness ($I_5$) of between about 0.25 µm and about 1.2 µm, about 0.5 µm and about 1.2 µm, about 0.25 µm and about 0.75 µm, about 0.60 µm and about 1.0 µm, and/or between about 0.40 µm and about 0.70 µm. In some embodiments, one or more of the layers 222, 223, 224 disposed between the outermost layer 225' and the innermost layer 221' have a thickness ($I_2$, $I_3$, $I_4$) of between about 0.5 µm and about 2.6 µm, about 0.8 µm and about 2.6 µm, about 0.5 µm and about 1.5 µm and/or about 1.0 µm and about 1.5 µm. In some embodiments, the entire coating 220 (e.g., the five-layer coating in FIG. 2) has a total thickness of between about 4 µm and about 8 µm, such as between about 4.5 µm and about 5.5 µm.

In some embodiments, the first three layers 221, 222, 223 each comprise a polyethersulfone. For example, such layers 221, 222, 223 may be greater than or equal to about 50%, about 60%, about 70%, about 80%, and/or about 90% polyethersulfone by weight. Such layers 221, 222, 223 may be substantially devoid of fluoropolymers and/or polyimides.

In other or further embodiments, the fourth layer 224 includes a polyamide-imide, a fluoropolymer (e.g., PTFE), and a polyimide that differs from the polyamide-imide. For example, the fourth layer 224 may include Torlon®, PTFE, and copolymer I. In some embodiments, approximately 5-50%, 7-30%, 8-25%, 9-20%, and/or 10-15% of a fourth layer 224 is, by weight, a polyimide that is not a polyamide-imide.

In other or further embodiments, an outermost layer 225' may include a fluoropolymer and a polyimide, such as copolymer I. An outermost layer 225' that includes both a fluoropolymer and a polyimide may differ in one or more respects from outermost layers that lack (or have relatively low amounts of) one or more of a fluoropolymer and a polyimide. For example, an outermost layer 225' that includes a fluoropolymer and a polyimide may have improved wear resistance, and/or durability relative to some other outermost layers. In some embodiments, an outermost layer 225' that includes a fluoropolymer and a polyimide may be sufficiently lubricious for delivery and/or withdrawal of a coated elongate medical appliance 200 into and/or from the vasculature of a patient. Stated differently, an outermost layer 225' that includes a fluoropolymer and a polyimide may have an average dynamic coefficient of friction that is comparable to or lower than that of (1) a PTFE-only outermost layer or (2) an outermost layer comprising a polymer blend of only PTFE and polyethersulfone.

In some embodiments, the inclusion of a polyimide in a layer 221, 222, 223, 224, 225 may enhance adhesion with an adjacent layer. For example, the addition of a polyimide to an outermost layer 225' may promote improved adhesion with an underlying layer, such as fourth layer 224. The inclusion of a polyimide (e.g., copolymer I) in other layers, such as fourth layer 224, may promote adhesion to an adjacent layer, such as third layer 223.

In some embodiments, the inclusion of a polyimide in a layer 221, 222, 223, 224, 225 may likewise improve cohesion within a layer 221, 222, 223, 224, 225. Stated differently, portions of a layer 221, 222, 223, 224, 225 that include a polyimide may be less likely to wear off due to chemical treatment and/or abrasive forces that are applied to the layer 221, 222, 223, 224, 225. The inclusion of a polyimide in a layer 221, 222, 223, 224, 225 may also reduce the amount of particulate that accumulates on a coating 220 as a result of manufacture of a coated medical appliance 200.

In some embodiments, the one or more layers 221, 222, 223, 224, 225 of a coating 220 are substantially devoid of metallic filler. For example, in some embodiments, the entire coating 220 is substantially devoid of metallic filler. In some embodiments, one or more layers 221, 222, 223, 224, 225 may lack abrasive material. For instance, in some embodiments, the entire coating 220 is substantially devoid of abrasive material.

The coated medical appliance of FIG. 2 may be manufactured in a manner analogous to the manner set forth above in connection with the medical appliance of FIG. 1.

EXAMPLES

A number of exemplary coatings were produced according to the present disclosure. The following examples are intended to further illustrate exemplary embodiments and are not intended to limit the scope of the disclosure. The data, in aggregate, support the conclusion that coatings with one or more outer layers that include a blend of PTFE and a polyimide (such as Copolymer I) may have one or more of a more uniform coloration, more uniform consistency (e.g., less "wrinkling"), increased scratch resistance, increased thermal stability, increased chemical resistance, increased coiling speed capability, and less susceptibility to straightening-related damage relative to coatings in which the outer layer of the coating does not include a blend of PTFE and a polyimide (e.g., coatings with outer layers of 100% PTFE).

Example 1—PTFE/Polyethersulfone Composition Lacking Copolymer I

A composition for forming an outermost coat was prepared by adding N-methyl-2-pyrrolidone (120 g) to a 795 gram composition that includes PTFE and polyethersulfone at a mass fraction of 7:3. The resulting composition was mixed until homogeneous.

Example 2—PTFE/Polyethersulfone Composition Including Copolymer I

Copolymer I (45 g) and N-methyl-2-pyrrolidone (120 g) were added to a 750 gram composition that includes PTFE and polyethersulfone at a mass fraction of 7:3. The resulting mixture was mixed until homogeneous, with no powder lumps visible to the naked eye.

Example 3—Polyethersulfone/Polyimide Compositions

Copolymer I (50 g) was added to a polyethersulfone composition (100 g) that included a colorant. The resulting composition was mixed until homogeneous, with no powder lumps visible to the naked eye.

Example 4—Polyamide-Imide/PTFE Composition with Copolymer I

Copolymer I (22.5 g) was added to 772.5 grams of a water-based binder that includes polyamide-imide and PTFE. The resulting composition was mixed until homogeneous.

Other polyamide-imide/PTFE compositions were made in an analogous manner, substituting the water-based binder with other water-based binders such as a polyimide-imide/PTFE/chromium oxide binder.

Example 5—PTFE/Copolymer I Compositions

Copolymer I (22.5 g) was added to 772.5 grams of a water-based topcoat that includes PTFE. The resulting composition was mixed until homogeneous.

Example 6—Four-Layer Coating without Copolymer I

A multi-layer coating was applied to a stainless steel hypotube (SS304 Hypotube; OD=0.670 mm) using a spool-to-spool process. The first coat was applied to the hypotube as the hypotube was drawn from a "payoff" spool and wound onto a "take-up" spool. More particularly, a polyethersulfone primer solution having a polyethersulfone content of about 15-40% was applied to the outer surface of the hypotube by passing the hypotube through a series of coating cups containing the polyethersulfone primer solution. Each cup included a round die that metered the volume of material that was applied to the hypotube. Once the polyethersulfone primer solution was applied to the hypotube in this manner, the hypotube was drawn through a multi-zone oven to remove solvent and cure the recently applied coat.

After the first coat had been applied and dried, a second coat of the same polyethersulfone primer solution was then applied to the exterior surface of the first coat in a manner analogous to that described above for the first coat. In applying the second coat, the round dies within the coating cups had a larger diameter than the round dies that were used when applying the first coat.

After the second coat had been applied and dried, a third coat of the same polyethersulfone primer solution was applied to the exterior surface of the second coat in a manner analogous to that described above for the first and second coats. The round dies within the coated cups that were used when applying the third coat had a larger diameter than the round dies that were used when applying the second coat.

After the third coat had been applied and dried, a fourth coat of the composition set forth in Example 1 was applied to the exterior surface of the third coat in a manner analogous to that described above. The round dies within the coated cups that were used when applying the fourth coat had a larger diameter than the round dies that were used when applying the third coat. After the final layer emerged from the oven, the entire coated hypotube was wound onto the "take-up" spool.

The total thickness of the resulting coating was 4.7 µm, with each layer having a thickness as follows: layers 1-3=1.4 µm each; layer 4=0.5 µm.

Example 7—Four-Layer Coating with Copolymer I

Coated hypotubes were manufactured as set forth in Example 6, with the following modifications. For the third layer, instead of applying the same polyethersulfone solution that had been used for the first and second layers, the composition of Example 3 was used. For the fourth layer, the PTFE/polyethersulfone/polyimide composition of Example 2 was used. After the final layer (i.e., fourth layer) emerged from the oven, the coated hypotubes were wound onto the "take-up" spool. The total thickness of the resulting coating was 4.7 µm, with each layer having a thickness as follows: layers 1-3=1.4 µm each; layer 4=0.5 µm.

Example 8—Five-Layer Coating Without Copolymer I

Hypotubes having a five-layer coating were manufactured by a process similar to that described above in connection with Examples 6 and 7. More particularly, the first three layers of the hypotube were applied to a SS304 hypotube (OD=0.670 mm) substantially as described in Example 6. For the fourth layer, a water-based polyamide-imide/PTFE binder was applied to the exterior surface of the third layer and dried using the multi-zone oven as described above. For the fifth layer, a water-based PTFE topcoat was applied to the fourth layer and dried with the multi-zone oven. The resulting coated hypotube was then subject to infrared radiation. The total thickness of the coating was 4.9 µm. The thickness of each layer of the coated hypotube was as follows: layers 1-3=1.25 µm each; layer 4=0.6 µm; layer 5=0.55 µm. Coated wires were also made by an analogous process.

Example 9—Five-Layer Coating with Copolymer I

Hypotubes having a five-layer coating were manufactured by a process analogous to that described above in connection with Example 8. More particularly, the first three layers of the hypotube were applied substantially as described in Example 6. For the fourth layer, one of the compositions of Example 4 was applied to the exterior surface of the third layer and dried using the multi-zone oven as described above. For the fifth layer, the composition of Example 5 was applied to the fourth layer and dried with the multi-zone oven. The resulting coated hypotubes were then subject to infrared radiation. The total thickness of each coating was 4.9 µm. The thickness of each layer of the coating was as follows: layers 1-3=1.25 µm each; layer 4=0.6 µm; layer 5=0.55 µm. Coated wires were also made by an analogous process.

Example 10—Biocompatibility of Example 7

The cytotoxicity of a coated hypotube of Example 7 was evaluated substantially as set forth in ISO 10993-5:2009(E) using L929 mammalian fibroblast cells (ATCC CCL1, NCTC clone 929). Under such conditions, the coated hypotube did not induce cytotoxicity (grade 0 score under the "qualitative morphological grading of cytotoxicity of extracts" grading system).

The hemolytic propensity of a hypotube of Example 7 was also evaluated. The hypotube was tested substantially as set forth in ISO 10993-4:2002, A1:2006 using fresh, whole rabbit blood. Under these conditions, the hypotube coating was determined to be non-hemolytic, as it exhibited an average hemolysis value of 5% or less.

Example 11—Coefficients of Friction

The lubricity of the outermost surfaces of hypotubes that had been coated as described in Examples 6 and 7 was examined using a Zwick 1120 tension tester. More particularly, a 350 mm section of coated hypotube was place in a pin vice that is connected to a Zwick 1120 machine. The hypotube was contacted by two blocks of PTFE material (having a contact surface of 25 mm in length) that provide 100 gram-force onto the coated hypotube. The coated hypotube was pulled through the PTFE blocks at a speed of 400 mm/min. As the hypotube is displaced at least 200 mm, the required pull force is measured. The average dynamic coefficient of friction value was the average pull force measured as the hypotube was displaced from 50 mm to 200 mm. The average dynamic coefficients of friction for each sample were as follows: Example 6=0.21; Example 7=0.15. For guidewires, the dynamic coefficients of friction were measured by coiling each guidewire around a stainless steel wire (0.43 mm). The resulting article was placed in the Zwick 1120 tension tester and tested as described above. The average dynamic coefficient of friction was 0.13 for a coating of a coated guidewire that had been coated in a manner analogous to that described in connection with the hypotubes of example 8. The average dynamic coefficient of friction was also 0.13 for a coating of a coated guidewire that had been coated in a manner analogous to that described in connection with the hypotubes of example 9.

Example 12—Passivation

Stainless steel hypotubes that had been coated as described in Example 6 and Example 7 were exposed to an aqeuous solution of citric acid (4-10% (w/w)) for approximately 30 minutes to investigate compatibility with potential passivation processes. For the stainless steel hypotube that had been coated as described in Example 6, substantial PTFE removal was observed by energy dispersive x-ray composition (EDX) analysis. In contrast, for a hypotube that had been coated as described in Example 7, significantly lower levels of PTFE removal were observed under similar conditions.

Example 13—Chemical and Mechanical Resistance—Isopropyl Alcohol

Figure 3:
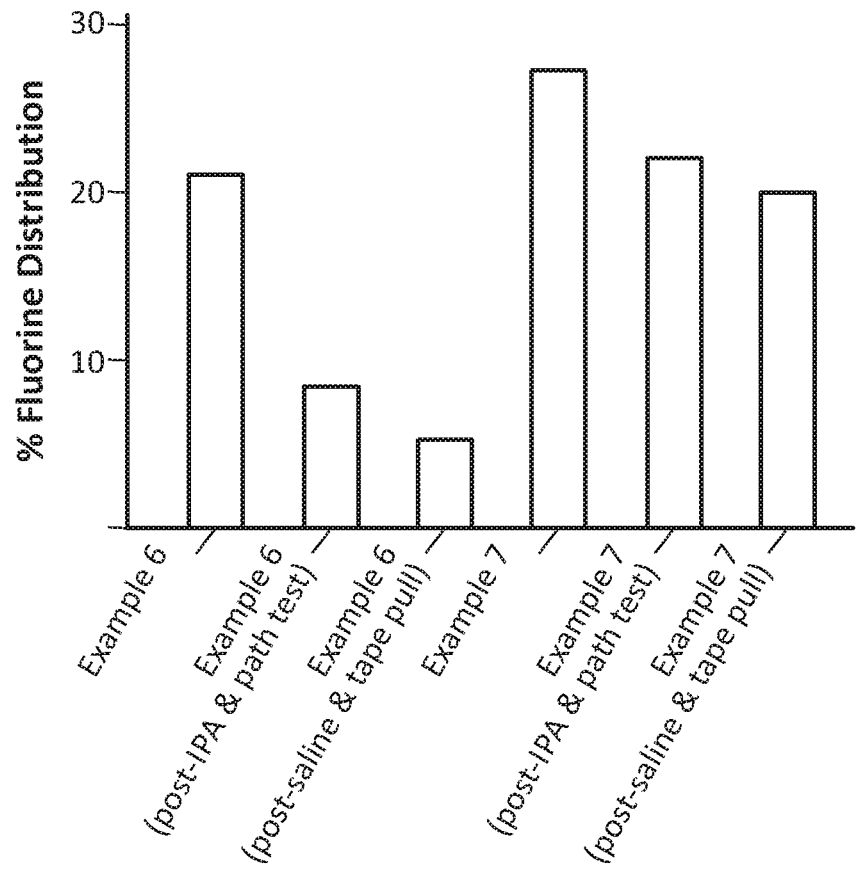
FIG. 3 is a bar graph depicting fluorine content for coatings of medical appliances under varying conditions.

Stainless steel guidewires that had been coated in a manner analogous to that described above for the hypotubes of Examples 6 and 7 were immersed in isopropyl alcohol (IPA) for 48 hours. The guidewires were then removed from the solution and repeatedly (5×) advanced along and retracted from an tortuous channel made from LDPE tubing. The fluorine content of the guidewires was analyzed by EDX (1) before the samples were immersed in isopropyl alcohol and (2) after the samples had both been immersed in isopropyl alcohol and repeatedly advanced into and retracted from the tortuous channel. The results of this experiment are shown in FIG. 3. The data show that the guidewires that had been coated as described in Example 7 were significantly more resistant to wear after exposure to isopropyl alcohol than guidewires that had been coated as described in Example 6.

Example 14—Chemical and Mechanical Resistance—Saline

Stainless steel guidewires that had been coated in a manner analogous to that described above for the hypotubes of Example 6 and Example 7 were immersed in saline for four hours. After the guidewires were removed, masking tape was applied to the outer surface of the guidewire and then removed. As can be seen from FIG. 3, guidewires that had been coated as described in Example 7 were significantly more resistant to wear after exposure to saline than guidewires that had been coated as described in Example 6 (compare column 3 with column 6).

Example 15—Straightening of Hypotubes

To straighten hypotubes that had been formed as described in Examples 6 and 7, the spooled hypotubes were straightened using a high-speed spinner with adjustable fingers that apply forces to straighten the hypotube. While defects (e.g., flaking of an outermost layer) were observed when straightening the hypotubes of Example 6, no damage was observed in connection with straightened hypotubes that had been coated as described in Example 7.

Example 16—Coiling of Wires

The performance of various coated wires under mechanical strain was examined by coiling the coated wires. For example, a first wire was coated with an exterior PTFE layer that did not include a polyimide. A second wire was coated with an exterior layer that included PTFE and a polyimide (e.g., Copolymer I). More particularly, using an Itaya point winding machine, 60 coils were formed from stainless steel wire (165 μm) that had been coated as described. No defect was found in any of the coils that were formed from the wire that had been coated with PTFE/polyimide. However, 38% of the coils that had been formed from the wire that had been coated without polyimide (e.g., Copolymer I) included one or more defects. Analogous results were obtained for other coated wires. In other words, coatings that included a PTFE/polyimide blend in the outermost layer(s) generally had a higher coil yield (i.e., more wires without defects) than coated wires with outer layer(s) made with PTFE and no polyimide. Additionally, coiling could generally be carried out at higher speeds for coated wires with a PTFE/polyimide blend in the outer layer(s) than for coated wires with outer layer(s) made from PTFE without a polyimide.

Example 17—Color Consistency

Coated wires were manufactured as described in Example 16. The coated wires that included polyimide (e.g., Copolymer I) had a more consistent color than those that did not include polyimide (e.g., Copolymer I). More specifically, coated wires that lacked polyimide (e.g., Copolymer I) were less consistent due to light shading or "tiger stripes."

Example 18—Fluorine Content

The fluorine content of various coated wires was assessed after the coated wires had been cured (e.g., IR irradiated) and/or sintered. The coated wires were sintered at various temperatures. The fluorine content of the wires was then measured by SEM/EDX. In general, the percentage of fluorine in the coatings of the coated wires that included polyimide (e.g., Copolymer I) was comparable to or greater than the percentage of fluorine in the coatings of coated wires that lacked polyimide (e.g., Copolymer I).

Example 19—Coil Shrinkage

Various coils of coated wires were placed in a coil reflow oven. Coils from coated wires that included polyimide (e.g., Copolymer I) shrank less, on average, than coils from coated wires that lacked polyimide (e.g., Copolymer I).

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A coating comprising:
 a first coating layer comprising a polyethersulfone; and
 a second coating layer comprising a polymer blend, the polymer blend comprising:
  a fluoropolymer;
  a polyimide; and
  a polyethersulfone;
 wherein the polymer blend comprises more fluoropolymer than polyethersulfone by dry weight, and
 wherein the first coating layer differs in composition from the second coating layer, wherein the coating forms an outer surface of a medical appliance, and wherein the medical appliance comprises a hypotube, a guidewire, a mandrel, or a stylet.

2. The coating of claim 1, wherein the fluoropolymer is polytetrafluoroethylene (PTFE).

3. The coating of claim 1, wherein the polyimide is an aromatic polyimide.

4. The coating of claim 1, wherein the polyimide comprises a subunit defined by Formula I:

Formula I

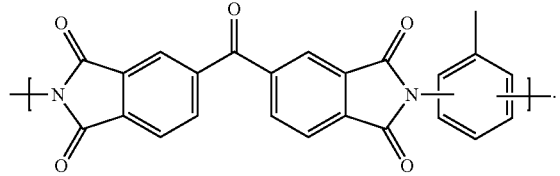

5. The coating of claim 1, wherein the polyimide comprises a subunit defined by Formula II:

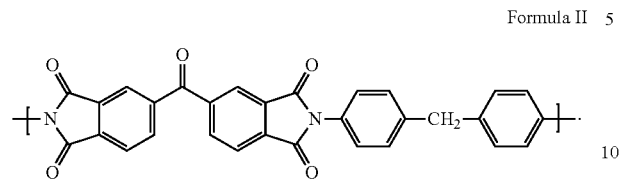

Formula II

6. The coating of claim 1, wherein the polyimide consists essentially of subunits defined by Formula I:

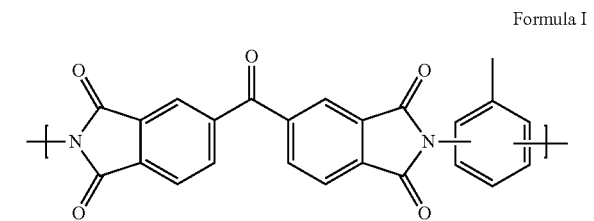

Formula I and subunits defined by Formula II:

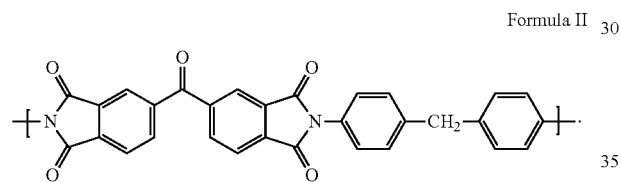

Formula II

7. The coating of claim 6, wherein the ratio of subunits defined by Formula I compared to the subunits defined by Formula II is between about 5:1 and about 3:1.

8. The coating of claim 1, wherein the polymer blend comprises between about 5% and about 50% polyimide by dry weight.

9. The coating of claim 1, wherein the polymer blend comprises between about 50% and about 95% fluoropolymer and between about 5% and about 50% polyimide by dry weight.

10. The coating of claim 1, further comprising a first intermediate layer that is disposed between the first coating layer and the second coating layer.

11. A multilayer coating for a medical device, the multilayer coating comprising:

a first coat comprising a polyethersulfone, wherein the first coat, when dried, comprises greater than 70% polyethersulfone by weight;

a second coat comprising a polyimide; and a third coat comprising a fluoropolymer and a polyimide;

wherein the first coat is an innermost layer and the third coat is an outermost layer of a coating on a medical device, and wherein the first, second, and third coats comprise compositions that differ from one another.

12. The multilayer coating of claim 11, wherein the medical device comprises a hypotube, a guidewire, a mandrel, or a stylet.

13. The multilayer coating of claim 11, further comprising a layer that is disposed between the first coat and the second coat.

14. The multilayer coating of claim 11, wherein the first coat is devoid of a fluoropolymer.

15. The multilayer coating of claim 11, wherein the third coat is thinner than any other layer of the multilayer coating.

16. The multilayer coating of claim 11, wherein the multilayer coating has a total thickness of between about 4 µm and about 8 µm.

17. The multilayer coating of claim 11, wherein the polyimide comprises:

a subunit defined by Formula I:

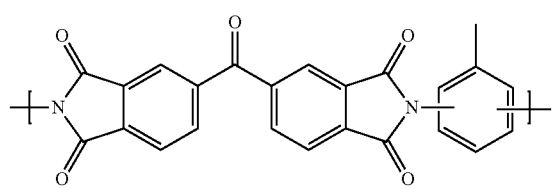

Formula I and a subunit defined by Formula II:

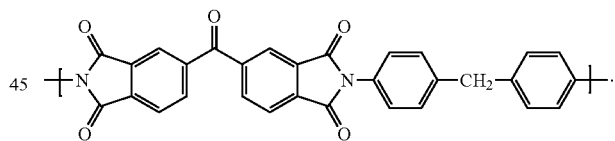

Formula II

18. The multilayer coating of claim 11, wherein the first coat adheres directly to a metallic alloy.

* * * * *